United States Patent [19]

Dodman et al.

[11] Patent Number: 5,314,888
[45] Date of Patent: May 24, 1994

[54] VETERINARY METHOD FOR TREATING INAPPROPRIATE ELIMINATION OF URINE IN HOUSEHOLD PETS

[75] Inventors: Nicholas H. Dodman, Grafton; Louis Shuster, Brookline, both of Mass.

[73] Assignee: Trustees of Tufts College, Medford, Mass.

[21] Appl. No.: 52,274

[22] Filed: Apr. 23, 1993

Related U.S. Application Data

[63] Continuation of Ser. No. 839,596, Feb. 21, 1992, abandoned.

[51] Int. Cl.$^5$ ............................................ A61K 31/495
[52] U.S. Cl. .................................................. 514/252
[58] Field of Search ........................................ 514/252

[56] References Cited

PUBLICATIONS

Malick, J. B., in *Current Developments in Psychopharmacology* vol. 5, 1979, pp. 1–27.
McMillen et al., *Eur. J. Pharma.* 160: 149–153 (1989).
McMillen et al., *Drug Dev. Res.* 12: 53–62 (1988).
Kozak et al., *Eur. J. Pharma.* 105:323–326 (1984).
White et al., *Pharma. Biochem. Behav.* 39:729–736 (1991).
Malick and Barnett, *Pharmacol. Biochem. Behav.* 5:55–61 (1976).
Olivier et al., in *International Academy For Biomedical and Drug Research*, vol. 1, 1992, pp. 67–79.
*Veterinary Pharmacology and Therapeutics*, 6th edition, Iowa State University Press, pp. 7, 259–269, and 303–305 (1970).
Olivier et al., *Psychopharmacology* 97:154–156 (1989).
Chemical Abstracts 106: 113426u, 1987.
Chemical Abstracts 108: 143285f, 1988.
Chemical Abstracts 115: 198360b, 1991.

*Primary Examiner*—Frederick E. Waddell
*Assistant Examiner*—Kevin Weddington
*Attorney, Agent, or Firm*—David Prashker

[57] ABSTRACT

The present invention provides a veterinary treatment method for animals suffering from a high arousal state. The treatment employs a class of pharmacologically active compounds having a pyrimidinyl-piperazine ring structure of which the most preferred member is buspirone. These compounds are administered to a variety of different domestic animals and household pets exhibiting behavioral problems which often are refractory to other modes of treatment.

8 Claims, No Drawings

VETERINARY METHOD FOR TREATING INAPPROPRIATE ELIMINATION OF URINE IN HOUSEHOLD PETS

This application is a continuation, of application Ser. No. 839,596, filed Feb. 21, 1992, now abandoned.

FIELD OF THE INVENTION

The present invention is concerned with the treatment of veterinary behavior problems commonly found in domesticated animals and household pets; and is particularly directed to the therapeutic treatment of living animals suffering from high arousal states and provides relief from these problems which are often refractory to other modes of treatment.

BACKGROUND OF THE INVENTION

Clinical behavior modification for domestic animals and household pets is a relatively new specialty in veterinary medicine and is poorly understood today by most practicing veterinarians. Prior to about 1974, the science of veterinary animal behavior was in its most rudimentary stages and the idea of treating specific behavioral problems in domesticated dogs and cats was still in its infancy. Subsequently, over the next approximately ten years (1974–1984) animal behavior modification focused mainly on behavioral shaping using techniques developed from the science of ethology (the study of innate animal behavior patterns) and similar conditioning strategies. Even in the mid-1980's the use of specific pharmacologically active substances to modify animal behavior was only just being explored and investigated. The outmoded psychopharmacological approach then employed was along lines popular in human medicine in the 1950's when neuroleptics such as chlorpromazine were first introduced for human psychotherapy. Only since about 1985 has the specific approach to pharmacologic modification of animal behavior disturbances been fully appreciated as being both possible and desirable.

The nature and depth of the problem is illustrated by a common behavioral problem in domestic cats—inappropriate elimination or urine marking. In the domestic cat, urine marking (or spraying) usually occurs in response to the stress of competition between cats; or in response to anxiety provoking interactions with people. This is a frustrating situation for cat owners; and, unfortunately, an incomplete resolution of this problem may, and often does, result in euthanasia of the cat by its owners.

It will be recognized and appreciated that the most common veterinary therapies to solve the behavioral problem of urine making include gonadectomy, environmental modification, and pharmacologic intervention [Borchelt, P. L., Compendium Continuing Education Pract. Vet. 8:197–205 (1986)]. Gonadectomy greatly reduces or stops urine marking; however, it has been reported that 10% of 134 castrated male cats and 5% of 152 spayed female cats continue to spray inappropriately following the surgery [Hart, B. L. and L. Cooper, Med. Assoc. 184:1255–1258 (1984)]. Moreover, cats are often refractory to both environmental and behavioral modification as a treatment for spraying or urine marking [Hart, B. L. and L. A. Hart, Canine and Feline Behavior Therapy, Lea & Febiger, 1985, p 134].

Among the different drugs presently prescribed as a treatment for urine spraying in cats are the progestins and the benzodiazepine, diazepam. Both of these drug therapies have had but limited success and are associated with undesirable side-effects for the animal. The progestins, medroxyprogesterone acetate and megestrol acetate, have been reported to eliminate urine marking behavior in approximately one-third of animals treated [Hart, B. L., J. Amer. Vet. Med. Assoc. 177:5229–533 (1980)]. Prolonged progestin therapy is also associated with recognized increases in appetite, body weight, and insulin levels. Progestins also have been reported to produce mammary gland hyperplasia, diabetes mellitus, acromegaly, pyometra, and adrenocortical suppression [Henik et al., Comp. Cont. Ed. Pract. Vet. 7:132–140 (1985)]. In comparison, diazepam has been shown to stop or reduce the frequency of spraying in neutered cats. However, side-effects of diazepam therapy include lethargy, temporary ataxia, and increases in appetite [Marder, A. R., Proceding of Animal Behavior Society Meeting, Raleigh, N.C., 1985]. Tolerance to the effects of the drug and physical dependence are also major problems associated with benzodiazepine therapy.

Accordingly, it is recognized and appreciated by veterinary practitioners and animal behavioral specialists that there remains a standing need for novel pharmacological treatments for a variety of animal behavior disturbances. Moreover, were a new class of pharmacologically active compounds to become available for clinical behavior modifications in domestic animals and household pets, this method would be of major advantage and maximum benefit both for the animal as well as its owner.

SUMMARY OF THE INVENTION

The present invention provides a veterinary method for treating living animals suffering from a high arousal state. One aspect of this veterinary method comprises the single step of:

administering to the living animal exhibiting a high arousal state a determinable dose of at least one pharmacologically active compound selected from the class consisting of N-[(4-heteroaryl-1-piperazinyl)alkyl]-substituted imides, its analogues and derivatives.

The present invention also provides another aspect of the veterinary method for treating living animals suffering from a high arousal state. This veterinary format comprises the multiple steps of:

administering to the living animal exhibiting a high arousal state a first dose of at least one pharmacologically active compound selected from the class consisting of N-[(4-heteroaryl-1-piperazinyl)alkyl]-substituted imides, its analogues and derivatives;

waiting a chosen time period for said first administered dose to reduce the high arousal state in the suffering living animal; and administering at least a second dose of said pharmacologically active compound to the suffering living animal.

DETAILED DESCRIPTION OF THE PRESENT INVENTION

The present invention is a veterinary method for treating and modifying the behavior of domestic animals and household pets suffering from a high arousal state or disorder. By definition, a high arousal state is a disturbed behavior or behavioral problem which typically presents itself as increased alertness, awareness, excitement, or fear and is often associated with increased cardiopulmonary and autonomic or purposeful activity. These problems often exacerbate and become refractory to conventional methods of treatment. A high arousal state includes and may take alternative forms of different behavior patterns and problems, many of which are associated with that species of animal or pet distinctively. Thus, a high arousal state includes and encompasses as least the following recognized behaviors: phobias including fear of other animals, of confinement, of inanimate objects, and of specific sounds or sights; aggression including aggression caused by overexcitement, overstimulation, and exceptional fear of other animals or people; inappropriate marking or spraying such as urinating on floors, walls, furniture, or persons; and elimination disorders such as inappropriate release of urine and feces in response to the presence of other animals or people. The term "high arousal state" is thus all inclusive of all these individual behavior problems and disorders, cumulatively and collectively.

The present veterinary methodology and manner of treatment is intended and expected to be widely used by veterinary practitioners to assist in the management of particular behavioral problems in several species of mammals and birds, typically domestic animals suffering from a high arousal state. Among the particular values and benefits provided by the veterinary treatment method are the following: (1) the effectiveness of the methodology in suppressing behavior problems associated with increased states of arousal; (2) the specificity of the pharmacologically active class of compounds employed for treating high arousal states; (3) the relative absence of undesirable side-effects to the animal being treated such as there being little or no drowsiness or ataxia as a consequence of therapeutic treatment; (4) the safety of the veterinary treatment method in that it is neither addictive nor habit forming for the animal and thus avoids any withdrawal symptoms commonly experienced with some other drug therapies; and (5) the permanent resolution of some behavioral problems following a limited course of treatment.

In order that the reader gain a proper recognition and appreciation of the present invention as well as to aid the reader in an easier and more complete understanding of the present veterinary treatment methods, the detailed description will be presented in sequential textual sections as the following: an identification and description of the pharmacologically active compounds as a class and some preferred formulations suitable for use when practicing the method; a description of representative behavioral problems in a variety of different animals when suffering from a high arousal state; a preferred protocol for the veterinary practitioner to follow; and a variety of representative clinical studies illustrating the effectiveness of the methodology as a whole.

I. The Pharmacologically Active Compounds Employed in the Method

The pharmacologically active compounds employed in this veterinary methodology are the N-[(4-heteroaryl-1-piperazinyl)alkyl]-substituted imide class of compounds developed in the early 1970's in the laboratories of Bristol-Myers. Compounds in this chemical class were developed for human use as effective tranquilizers lacking the sedative or anti-adrenergic side-effects commonly associated with the phenothiazines previously known. The development of this class of drugs employed a range of different biological screens and test systems to identify those formulations which had a minimum of depressive side-effects. As research studies reported in the scientific literature demonstrate, this class of composition was employed for treatment of anxiety disorders in humans; provided a class of "anxiolytic" compositions; and functioned as serotonin agonists at 5-hydroxytryptamine receptors in the brain, thereby effectively treating anxiety states without concomitant sedative, muscle relaxant, or anticonvulsant activities. The discovery and development of this class of pharmacologically active compounds are well known in the pharmaceutical and scientific literature and are represented by the following: New, J. S., *Medical Research Reviews* 10:283-326 (1990) and the references cited therein; Goa, K. L. and A. Ward, *Drugs* 32:1114-129 (1986) and the references cited therein; Taylor, D. P., *FASEB J.* 2:2445-2452 (1988) and the references cited therein; Tunnicliff, A., *Pharmacol. and Toxicol.* 69:149-156 (1991) and the references cited therein; *Buspirone: Mechanisms and Clinical Aspects*, Academic Press, San Diego, Calif. 1991. The text of each of these publications individually is expressly incorporated by reference herein both for their technical content and information as well as for their historical perspective and analysis.

It will be recognized and appreciated that the actual membership of the class collectively comprising the N-[(4-heteroaryl-1-piperazinyl)alkyl)-substituted imide compounds is unusually large and diverse. As documented and reported particularly within the J. S. New publication [*Medicinal Research Reviews* 10:283-326 (1990)], the presently known methods of synthesis provide a wide and diverse variety of analogs, derivatives, and substitutions - each of which are pharmacologically active in varying degree. Thus, for descriptive purposes only, it is desirable to address only a few specific formulations as the best representative embodiments illustrative of the class and membership as a whole. Probably the best known formulations and embodiments are thus those listed within Table 1 below; and among these preferred formulations, buspirone is undoubtedly the best known.

TABLE 1

| Compound Name | Structure |
|---|---|
| buspirone | 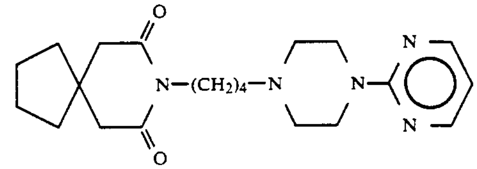 |

TABLE 1-continued

| Compound Name | Structure |
|---|---|
| gepirone | [structure: 4,4-dimethyl-2,6-dioxopiperidine-N-(CH2)4-N-piperazinyl-pyrimidine] |
| ipsapirone | [structure: benzisothiazole-1,1-dioxide-N-(CH2)4-N-piperazinyl-pyrimidine] |
| SM-3997 | [structure: norbornane dicarboximide-N-(CH2)4-N-piperazinyl-pyrimidine] |
| WY-47,846 | [structure: tricyclic dicarboximide-N-(CH2)4-N-piperazinyl-pyrimidine] |
| MOL 72832 | [structure: spiro[4.5]decane-dione-N-(CH2)4-NH-CH2-benzodioxole] |

For purposes of clarity and ease of comprehension, the remainder of this description will confine itself to buspirone as the composition of choice and it will be identified alone without reference subsequently in the various procedures, protocols, and clinical histories provided. It will be recognized and explicitly understood, however, that the confinement of this descriptive text to the use of buspirone and its treatment effects are merely representative of the entire membership of the pharmacologically active compounds, cumulatively and collectively, as a class. All that is explicitly said regarding buspirone is clinically applicable to all other analogs, derivatives, and substitutions, albeit in varying degrees of potency and effectiveness.

Buspirone is derived from the N-[(4-heteroaryl-1-piperazinyl)alkyl]-substituted imide class of compounds. The chemical name of buspirone ($C_{21}H_{31}N_5O_2$) is 8-442-pyrimidinyl-1-piperazinyl butyl-8-azaspiro-45-decane-79-dione and its structural formula is illustrated by Table 1. It was initially designed as a psychosedative without the side-effects of sedatives, such as the phenothiazines; and the success of early testing in experimentally-induced paradigms of human stress states in laboratory animals led to clinical trials for treating anxiety and stressful conditions in humans. Buspirone lacks affinity for the benzodiazapine receptor and has weak dopamine blocking activity but its main mechanism of action is thought to be due to its strong binding and agonistic properties at the serotonin (5HT) 1A receptor.

Buspirone is presently manufactured (Bristol-Myers) for the treatment of human anxiety-related disorders and is supplied as 5 mg or 10 mg tablets to be taken orally. This preparation and this size of tablet (5 or 10 mg) is the preferred preparation for use in the treatment of animals suffering from potentially responsive high arousal states. The 5 mg tablet, either halved or whole, is the preparation normally used for cats or small dogs and the 10 mg tablet is used for larger dogs or horses. If desired, an injectable preparation in saline is easily made for intramuscular or intraperitoneal administration on single or multiple use occasions. Other preparations can be easily made for administration via skin (transdermal), via mucous membrane application, or per rectum.

The most suitable use of buspirone is as a psychopharmacological adjunct to conventional behavioral therapy to treat potentially responsive behavioral problems or disorders in domestic or pet animals. It is expected that buspirone (as well as 5 other members of the class) will be found most useful in the treatment of disorders such as inter- or intra-species aggression, excessive fear of circumstances, people, or other animals, and treatment of the inappropriate or excessive responses to primitive drives such as territoriality.

The main advantages of buspirone and this chemical class as a whole over other pharmacological adjuncts to behavioral therapy are:

a. its effectiveness (it can be effective where other compounds fail);

b. its specificity (that it produces the desired response without obvious changes in the level of consciousness and without producing ataxia, increases in appetite, or other side-effects);

c. that it is non-addictive, non-habit forming, and is not associated with withdrawal (which can further exacerbate stress);

d. that it has a high therapeutic ratio and is extremely safe; and e. permanent resolution of some behavior problems following a limited course of treatment.

II. The Veterinary Methodology

The preferred treatment process is to be conducted as follows:

1. First of all establish by reference to the clinical history and examination (including laboratory tests, if necessary) that the animal is suffering from a behavioral disorder which results from a state of high arousal (from whatever cause).

2. Inform the owner of the nature of the condition including, where possible, an identification of the causative events or factors.

3. Outline environmental and management alterations (including dietary manipulations) which may be useful as supportive therapy.

4. Outline to the owner any specific behavioral modification therapy, such as counter-conditioning or desensitization to the aversive stimulus, as may be indicated.

5. Explain the benefits of adjunctive pharmacologic therapy if this is appropriate, i.e., if the condition is unlikely to respond to conventional behavioral treatment alone or if the response to this type of treatment is likely to be protracted or inconclusive.

6. With the owner's full understanding, the pharmacologic therapy is started using dose rates of up to 1-3 mg/kg of body weight of buspirone (or an equivalent dose of any other class member) given orally two or three times daily.

7. The owner is instructed to initiate behavior modification therapy and institute certain management strategies in conjunction with the pharmacologic treatment in most cases.

8. The owner should keep careful notes of the frequency of the unwanted behavior and intensity of the response on a daily basis. Observations of the animal's general state of arousal (calm, excited, agitated, etc.) should also be made including a careful watch for side-effects (although these are uncommon).

9. The owner should be given a telephone number and veterinary contact name in the event of any questions arising during treatment.

10. The owner should be instructed to contact the veterinary clinician weekly during treatment.

11. If initial treatment appears ineffective or is only partially effective, and if there are no notable side-effects, the dose rate can be increased weekly until an effect approaching the desired effect is obtained. Treatment is discontinued if at doses of 1-2 mg/kg of body weight there is no response or if at lower doses there are any untoward effects.

12. Owners should be instructed at the beginning of the course of treatment that the medication is not immediate in its effect and that a minimum of 3-5 days, and sometimes up to a week, is necessary to observe the effects of a change in dose rate; and that once achieved, continued improvement will be seen over a period of about 3 weeks in most cases.

13. The course of treatment is continued preferably for 1-2 months at the optimal dose. The dose is then gradually reduced to permit gradual acclimation to the circumstances or events which were previously perceived as unfavorable. This gentle weaning off insures that the animal is gradually habituated (desensitized) to increasing intensities of the arousing stimulus. Finally, the non-medicated animal can be confronted with the event or situation which previously induced the arousal response with less chance of the exaggerated response previously noted.

14. If the animal shows signs of returning to a high arousal state during the weaning off process, the dose of the drug should be increased again to the previously effective level for an additional 1-2 months or more.

15. Animals can be kept on buspirone indefinitely; but it is good practice and preferable to attempt to withdraw the medication at intervals depending on the case. The result of such treatment will be one of the following: (a) a permanent resolution of the problem, even when medication is withdrawn; (b) a resolution of the problem while on medication; (c) partial resolution of the problem; or (d) no response to treatment in which case alternative treatment strategies should be pursued.

Under- and Overdosage Effects

If buspirone treatment is given at sub-optimal dose rates in a condition which would otherwise be responsive, the response may be so mild as to be inapparent and the clinical impression would be that the treatment was ineffective. If the buspirone is given at doses greater than those recommended, there are unlikely to be any serious untoward effects. It follows that buspirone is very safe for normal usage in animals although side-effects and limitations and even contraindications (hypersensitivity to buspirone) have been listed for human patients (see Drug Facts and Comparisons, 1992 edition, pages 1208-1211). Side-effects are generally expected to be more common at the higher end of the dose scale.

Range of Dosage Normally Given

For small animals (dogs and cats) the desirable dose range is from 1.25 to 30.0 given twice or three times a day by mouth in tablet form. For large animals such as horses, the dosage would be considerably higher and is in the range of 30-70 mg given three times a day by mouth.

The medication is presently supplied commercially in pill form; and 5 mg and 10 mg tablets are available. Cats would generally be started on 2.5 mg given twice a day for a one month course of treatment. Thereafter, the condition is reassessed. Treatment may then be continued at the same dose rate for an additional month or more; or until the behavior is under control; or until it is obvious that the treatment is not working for that cat. On occasion, cats have been started on lower dosages than this, typically in the range of 1.25 mg given twice daily, but these dosages have been increased up to 10 mg three times a day in some felines who have showed only partial response to the lower dosages.

In dogs, treatment is usually started with 5 mg of buspirone given two or three times daily, although larger dogs (heavier than 20 kg) may be started on 10 mg given three times a day. As with cats, the dosage is increased if necessary (if the response is suboptimal) and dosages as high as 30 mg three times a day have been used in larger dogs.

Large animals, like horses, are started on 30 mg of buspirone given three times daily by mouth. This dose rate is then increased at 10 mg per dose per day until a maximum of about 70 mg three times a day is reached, although higher doses would probably be well tolerated.

III. High Arousal States Suitable for Treatment

A variety of different clinical conditions and behavioral disorders would benefit from veterinary treatment with buspirone or any other member of the class of compounds. The following are merely representative and illustrative of the most commonly encountered behavioral problems.

A. High arousal states in horses (situational phobias including fear of confinement, inanimate objects, sights, and sounds).

Irrational fears or hatreds, known as phobias, are common throughout the animal world. These fears probably arise by failure of normal habituation to a particular situation or circumstance as a result of an unpleasant experience gained in that particular situation or circumstance on at least one occasion. Because of the high arousal, which itself is unpleasant, the phobia becomes self-propagating and intensifies. By temporarily altering the animal's perception of the phobic experience to make the experience less stressful, successful drug therapy will, in time, cause the animal to become desensitized to the stressful situation or events.

B. High arousal states in dogs.

Phobias

Dogs develop phobias for the same reasons as horses or other animals. Phobias are excessive or untoward reactions to a particular stimulus. Particularly common in dogs is a fear of people, which may cause the dog to withdraw and hide while manifesting clinical signs of increased arousal associated with activation of the fright or flight mechanism. In other individuals, this fear produces a paradoxical response in that the dogs become aggressive. Examples of other phobias include fear of other animals, e.g., other dogs; fear of being left alone (separation anxiety); and fear of certain sensory stimuli such as wind noise, static electric shocks, and the noise of fireworks. To date, several different phobias in dogs have been treated, with varying degrees of success.

Aggression

High arousal aggression is one of the four major categories of aggression in human beings and a similar classification system is applicable in dogs. Dogs prone to this type of aggression may become exceptionally aggressive when excited or frightened as they seem to become overstimulated and overaroused to the point where they cannot control their behavior, even when instructed by their owners. Examples of this type of aggression are provided by certain highly excitable, overactive, or hyperkinetic dogs with dominant or fearful dispositions. The use of buspirone under these circumstances will decrease arousal with a concomitant decrease in arousal-related aggression.

Inappropriate Marking Behaviors in Dogs

When dogs become aroused as a result of environmental stress, they may manifest their tensions by marking their territory. Unfortunately for the owners, this involves leg lifting and squatting marking behavior with associated urination or defecation on floors, furniture, or vertical surfaces. Decreasing arousal with buspirone will reduce or eliminate this unwanted behavior.

C. High Arousal Conditions in Cats

Phobias

Cats, like horses, and dogs, also develop phobias and for the same reasons. The general triad of fear applies here in that cats may be frightened by animate objects, situations, or inanimate stimuli and will clinically manifest an exaggerated response to the phobic stimulus by fight or flight associated with increased arousal. Decreasing the overall arousal level and stabilizing the underlying mood of the cat helps to reduce the intensity of all of these phobias.

Aggression

Aggression in cats can be either offensive (the quiet, biting attack) or defensive (affective defense behavior). Both types of aggression respond to buspirone. From the theoretical viewpoint, affective defense behavior should respond best, because offensive aggression is relatively unemotional. Clinical results, however, have indicated that both types of aggression respond well.

Elimination Disorders

Inappropriate elimination of urine and feces is the most common behavior problem in the cat. Urine marking usually occurs in response to the stress of competition between cats or in response to anxiety provoking interactions with people. Probably because urine marking in cats is associated with increased arousal, buspirone, by its actions, appears to be an appropriate drug for this problem. Buspirone has eliminated or substantially reduced marking in treated cats.

IV. Clinical Studies and Case History Reports

Case 1

An adult horse was presented to the Medicine Department of Tufts University School of Veterinary Medicine for evaluation and treatment of a behavioral problem. The problem was that the horse, when confined inside a building in a stall, would become extremely agitated and aroused by the sound of rain falling on the roof, by wind noise, and by the sound of thunder. Reportedly, the problem was much worse in stalls with low roofs and manifested as extreme excitement, including bucking, rearing, whinnying, and pacing to the point where the animal would damage itself by colliding with the walls of the stall. The horse had previously been in a barn which collapsed during a storm when lightning struck the building; and this was believed to be the likely cause of the high arousal noted under similar circumstances.

On physical examination, the horse appeared to be in good condition apart from some minor abrasions on the skin. Buspirone was selected as the treatment of choice, being most likely to reduce arousal without causing serious side-effects. Treatment was started cautiously, giving 30 mg of buspirone three times daily; and the dose rate was increased by 10 mg per dose per day until the total daily dose reached 210 mg. There were no side-effects at this dose and the animal was maintained on buspirone at this dosage from the remainder of its two week stay in the hospital. Toward the end of the two week period, the clinician in charge had occasion to contact personnel on duty during a violent storm to which the horse would normally have been expected to show signs of arousal and fear. The observer reported that the horse was standing quietly and in a composed manner, apparently undisturbed by the storm. The horse was later discharged back to the owner with medication to be continued for an additional two weeks.

In the last report received (some weeks after medication had been discontinued), it was stated that the horse continued to maintain its improvement—being undisturbed by wind noise, rain noise, the noise of thunder or low roofs. The buspirone treatment was considered a success by all persons involved.

Case 2

An eight month old male Doberman Pinscher was presented to the behavior clinic of Tufts University School of Veterinary Medicine with the primary complaint being a fear of strangers, especially of judges in the show ring. The dog was very well trained—but sometimes when being inspected by a judge, would lose his composure, break his stance, and move away from the judge. There was no apparent explanation for this behavior; although the likelihood is that the dog had been frightened or hurt at some time previously by a person who looked like or behaved like a competition judge. Judges who initiated the behavior were men wearing dark clothes, and the problem typically occurred when the judge moved towards the rear end of the animal. Desensitization and counter-conditioning behavioral modification therapy had already been tried and it was recommended that this be continued. In addition, treatment with buspirone (5 mg given orally three times a day for 30 days) was initiated. During the month of treatment, the dog was entered for at least one show and showed no signs of fear when approached by the judge. The dog was placed highly in the competition. As a consequence, it was hoped that the dog would be permanently desensitized to the aversive stimulus (the judge) if it once learned to tolerate the challenge without fear. In this case, however, the animal's fear returned when the buspirone medication was discontinued and fear was evidenced at subsequent shows. Buspirone medication was reinstituted for a longer period (2 months) and whilst on medication, the dog was fine. But in each instance when medication was withdrawn, mild fear returned and a permanent improvement was not effected. This case demonstrates the effectiveness of buspirone at reducing the dog's arousal level and, therefore, reaction during judging; but in this case the fear was so ingrained that it returned on each occasion when buspirone medication was discontinued.

Case 3

A seven year old German Shepherd bitch was presented to the behavior clinic with multiple phobias involving a variety of sounds. Apparently, the dog's reaction to sounds had become problematic when the owners moved to a new house some months earlier. The dog reacted particularly badly to the noise of wind and rain and thunder; but was also frightened by the noise of backfiring cars, fireworks, and of being left alone, particularly at night. The owner had to sleep downstairs at night on a couch with the dog on leash next to her, as when she retired to bed upstairs the dog would pace and whine and disturb the household throughout the night. Treatment with buspirone was initiated at a dose rate of 10 mg given three times a day by mouth for a period of thirty days. The dose rate had to be increased over time because of a partial response involving a diminution in reactions to miscellaneous sound and mild wind noise; and the dose ultimately reached was 30 mg given three times a day. At this point, the dog seemed generally much calmer and more composed and could tolerate even moderate wind and rain noise and distant thunderstorms. Unfortunately, before the desensitization process was complete a large electric storm directly over the house caused the animal to lose its composure and much of the progress which had been achieved was lost. Subsequently, further administrations of buspirone and some behavior modification therapy produced only minor improvements in the animal's response to the fear-inducing stimuli; and the treatment was considered to be only partially effective.

Case 4

A 3 year old Lhasa Apso bitch was presented at the behavior clinic of Tufts University School of Veterinary Medicine with a history of aggression directed towards a baby and inappropriate elimination of urine and feces in the home. Both problems had started when the baby started to walk; and, anthropomorphically speaking, would appear to have been caused by jealousy which made the animal anxious, aroused, and hostile. The primary treatment was buspirone, 5 mg, to be administered twice a day for a month. Some minor adjustments in management were also made such as feeding the dog twice daily rather than ad lib; and suggesting that the dog should be brought on walks with the baby. The owners reported that, while on buspirone medication, the dog's aggression towards the baby was abolished and that inappropriate elimination behavior was substantially reduced. The buspirone treatment was extended for an additional month, but then buspirone was withdrawn completely. The owners reported that during the treatment phase the dog had appeared to be slightly sedated and would not, for example, run to greet them at the door when they came home. When the buspirone was withdrawn, the aggression did not return but there was still some inappropriate elimination occurrences indicating incomplete desensitization. The owners did not wish to continue with the buspirone medication; however, they were very pleased with the degree of behavioral change which had been made.

Case 5

A 7 year old spayed female German Shorthaired Pointer was presented at the behavior clinic of Tufts University School of Veterinary Medicine with the primary complaint being that the dog showed aggression to children. After careful questioning of the owner, it was ascertained that this aggression was related to fear and high arousal in the presence of children; and probably stemmed from some unpleasant encounters at an earlier time. The owners were given some recommendations as to how to handle the dog to prevent biting incidents. The dog was also treated with buspirone, 5 mg, to be given twice a day for a month. The buspirone treatment was subsequently extended so that the dog eventually received a two month course of treatment. From the time the medication was started there were no further incidents of aggression and a distinct calming effect was noted for the animal commencing approximately three weeks after the buspirone treatment was initiated (corresponding with what would be the peak action time of the drug). Problems of aggression at the front door with people visiting and aggression to other dogs in the street were also eliminated. Towards the end of the second month of treatment, the dog became depressed and was diagnosed with leukemia. This condition had obviously been present for some time but was not escalating. The simultaneous presence of leukemia confuses the interpretation of the results of treatment but the owners were convinced that the medication helped and that the dog was calmer as a result.

Case 6

A castrated male cat (age unknown) was reported to be showing extreme aggression towards three other cats and two dogs in the home. The aggression was manifested as unrelenting attacks involving stalking, scratching, biting, and vocalizing. The cat was treated with buspirone, 2.5 mg, twice a day by mouth for 16 days. For the first twelve days of treatment the cat was kept separate from the other animals in the home but was then reintroduced to the other animals by confining it in the kitchen and allowing it to interact with them. Aggression was considered to be considerably reduced and reached the point where the other resident animals could enter the subject's confinement area without being attacked or even acknowledged. Medications were discontinued four days after this reintroduction period and the cat was observed for signs of returning aggression. Aggression had returned to pretreatment levels three to four weeks after the discontinuation of treatment and the owner asked for the cat to be put back on medication. This was done but the results of this second course of treatment are not yet available.

Case 7

A 9 year old spayed female domestic long-haired cat was presented at the behavior clinic with a history of inappropriate elimination of urine and feces. After careful questioning of the owner and examination of the cat it was determined that there was a psychogenic origin to this unwanted marking behavior and that it was caused by high arousal. The problem had started coincident with a boyfriend moving into the owner's apartment at which time the cat had come skittish and withdrawn. Medication with buspirone (2.5 mg twice a day by mount for one month) was initiated and the owner was asked to report back to the clinician (NHD) at intervals. The results of treatment were spectacular. Within a few days, the cat appeared to be much more friendly and back to her usual sociable self. She would greet both the owner and the boyfriend when they came to the door and would lie around in their presence purring and contented. The inappropriate elimination behavior stopped and the cat's behavior was, in general, described as more kittenish and playful. This improvement was maintained when the medication was discontinued.

Case 8

A 5 year old spayed female Siamese cat called "Mai Tai" was presented at the behavior clinic of Tufts University School of Veterinary Medicine with a history of aggression directed towards the other cat, "Saki," in the home. Mai Tai was always the aggressor and she would stalk around the house looking for the other cat and then attack it. The fights, which had been going on for a year (since Mai Tai was 4 years old) were violent and involving whining, hissing, and the cats rolling around on the floor grappling with each other. The precipitating event for these attacks was Mai Tai's inadvertently being let out into the garden (she was normally an indoor cat); and so the diagnosis was that of redirected aggression. Medication for both cats with buspirone was initiated. Both cats were prescribed 1.25 mg of buspirone twice a day for a month. In a follow up telephone conversation one week later, the owner reported "amazing progress." The cats appeared friendlier within a day or two of the initiation of buspirone therapy and were able to interact socially. There were only minor incidents, such as when Mai Tai started to chase Saki but only in a half-hearted way. At these times, Saki did not seem to care and the whole situation came to nothing. The owner, who was jubilant, was advised to continue medication and stay in touch. Two weeks later the owner reported that for the last 10 days there had been no incidents at all and that Mai Tai had been much more playful than usual ("Back to being as playful as when she was a kitten."). After two more weeks there had been a couple of minor incidents but otherwise all was considered to be well. The cats were still on buspirone, but the owner admitted that she may have omitted a couple of doses. Two months later the owner recontacted the clinician and reported that there had been no further incidents. She was very pleased at the result so treatment. The cats had been off medication for four or five weeks at this time and had remained friendly with no aggressive incidents noted at all.

Case 9

A 10 year old castrated male cat was brought to the clinic of Tufts University School of Veterinary Medicine with a one year history of urine spraying (territorial marking). The initiating factor had been the arrival of a Siamese cat (female, neutered) into the male cat's territory when the owner's parents came to stay. Urination, in the form of spraying on the furniture, was noted at least once a day despite the provision of excellent litter box facilities. On examination, the cat was noted to be frightened and skittish; and its easily arousable nature was thought to be a factor in the condition. The cat was medicated with buspirone (2.5 mg twice a day by mouth for a month). Ten days after the start of treatment there had been only one spraying incident, a marked improvement of the previous situation. Two other incidents were reported over the next three weeks; and at the time of reporting, there had been no incidents for ten days. At about this time, the owners had a change of heart in terms of how best to manage this problem and decided to make the cat an outdoor cat by allowing it free access to the garden. On the long-term follow up five months later, the cat was no longer urinating in the house.

The present invention is not to be restricted in form nor limited in scope except by the claims appended hereto.

What we claim is:

1. A veterinary method for treating inappropriate elimination of urine in household pets such as dogs and cats, said veterinary method comprising the step of:
    administering to the household pet which is eliminating urine inappropriately an effective amount of at least one pharmacologically active compound selected from the class consisting of N-[(4-heteroaryl-1-piperazinyl) alkyl]-substituted imides, its analogues and derivatives.

2. A veterinary method for treating inappropriate elimination of urine in household pets such as dogs and cats, said veterinary method comprising the steps of:
    administering to the household pet which is eliminating urine inappropriately a first effective amount of at least one pharmacologically active compound selected from the class consisting of N-[(4-heteroaryl-1-piperazinyl) alkyl]-substituted imides, its analogues and derivatives;
    allowing sufficient time for said first administered effective amount to begin to reduce the inappropriate elimination of urine by the household pet; and
    administering a second effective amount of said pharmacologically active compound to reduce further the inappropriate elimination of urine by the household pet.

3. The veterinary method as recited in claim 1 or 2 wherein said administered pharmacologically active compound is buspirone.

4. The veterinary method as recited in claim 1 or 2 wherein said administered pharmacologically active compound is gepirone.

5. The veterinary method as recited in claim 1 or 2 wherein said administered pharmacologically active compound is ipsapirone.

6. The veterinary method as recited in claim 1 or 2 wherein said administration is oral.

7. The veterinary method as recited in claim 1 wherein said administration is repeated on multiple occasions.

8. The veterinary method as recited in claim 1 or 2 wherein said administration is one selected from the group consisting of transdermal, rectal, mucous membrane, intramuscular, and intraperitoneal administrations.

* * * * *